(12) United States Patent
Lischka et al.

(10) Patent No.: US 6,509,474 B1
(45) Date of Patent: Jan. 21, 2003

(54) METHOD OF LITHIATING FIVE MEMBERED HETEROCYCLES

(75) Inventors: Uwe Lischka, Frankfurt am Main (DE); Dieter Hauk, Friedberg (DE); Peter Rittmeyer, Sulbach/Ts. (DE); Ulrich Wietelmann, Friedrichsdorf (DE)

(73) Assignee: Chemetall GmbH, Frankfurt a.M (DE)

( * ) Notice: Subject to any disclaimer, the term of this patent is extended or adjusted under 35 U.S.C. 154(b) by 0 days.

(21) Appl. No.: 09/830,424

(22) PCT Filed: Oct. 21, 1999

(86) PCT No.: PCT/EP99/07985

§ 371 (c)(1),
(2), (4) Date: Jul. 20, 2001

(87) PCT Pub. No.: WO00/24732

PCT Pub. Date: May 4, 2000

(30) Foreign Application Priority Data

Oct. 26, 1998 (DE) .......................................... 198 49 197

(51) Int. Cl.⁷ .................... C07D 333/08; C07D 307/28; C07D 277/22; C07D 209/08

(52) U.S. Cl. .......................... 548/400; 548/452; 549/29; 549/429; 260/665 R

(58) Field of Search ...................... 260/665 R; 548/400, 548/452; 549/29, 429

(56) References Cited

FOREIGN PATENT DOCUMENTS

| GB | 1 227 425 A | * | 4/1971 |
|---|---|---|---|
| GB | 2 067 997 A | * | 8/1981 |
| WO | 98/57974 A | * | 12/1998 |

OTHER PUBLICATIONS

Screttas, et al, 1974, Journal of Chemical Society, 745–748.*
Eisch, et al, 1962, Journal of Organic Chemistry, 27(11) 3745–3752.*

* cited by examiner

Primary Examiner—Joseph K. McKane
Assistant Examiner—Andrea D. Small
(74) Attorney, Agent, or Firm—Antonelli, Terry, Stout & Kraus, LLP

(57) ABSTRACT

The invention relates to a method of lithiating CH-acidic five-membered heterocycles whereby the five-membered heterocycle is reacted with metallic lithium in an ether-containing solvent in the presence of an H acceptor.

13 Claims, No Drawings

METHOD OF LITHIATING FIVE MEMBERED HETEROCYCLES

This application is a 371 of PCT/EP99/07985, Oct. 21, 1999.

This invention relates to a method of lithiating CH-acidic five-membered heterocycles, wherein the five-membered heterocycle is reacted with metallic lithium in an ether-containing solvent in the presence of an H acceptor. The invention also relates to a use of the products of the method.

Hydrocarbons are more readily metalated the higher their CH-acidity, the more electropositive the metal, the larger the active surface area of the metal and the more polar the solvent. In this way alkynes, cyclopentadiene (and derivatives) and, for example, triphenylmethane can be deprotonated by means of alkali metals. The problem, however, is that secondary reactions such as, for example, hydrogenations and/or CC-splitting, lead to poor yields. These secondary reactions become prominent particularly in highly polar solvents (for example, hexamethylphosphorous triamide (HMPT), 1,2-dimethoxyethane (1,2-DME)) or protic solvents (for example, $NH_3$). On the other hand, in solvents which are not highly polar (for example, benzine, ether), the reaction rate is too-low to enable the direct metalation principle to be widely utilised. Thus, for example, the metalation of triphenylmethane with potassium in boiling 1,2-DME requires 10 hours. Caesium is a special case since, for example, it reacts quantitatively with toluene at relatively elevated temperatures to form insoluble benzylcaesium.

Five-membered heterocycles have a considerably lower CH-acidity than do alkynes and cyclopentadienyls and are therefore harder to metalate. Thus furan yields only small quantities of furan-2-carboxylic acid following reaction with potassium or K/Na alloy and subsequent derivatisation with $CO_2$. Thionaphthene which has been activated by benzoanellation reacts with Na and, after reaction with $CO_2$ and $H_2O$, produces the derivatisation product in moderate yield:

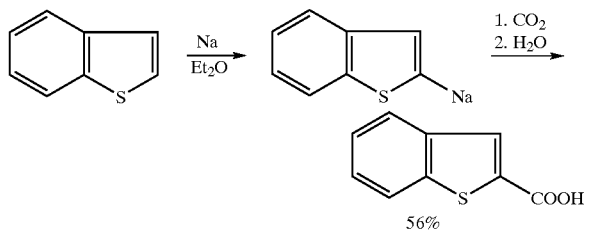

It may be assumed that the poor yields are the result of double-bond hydrogenation.

Thiophene itself reacts with a lithium metal dispersion in THF only very slowly and with moderate yields. After a reaction time of one week, a conversion of only 12% was observed by von Screttas (C. G. Screttas, J. C. S. Perkin Transactions II, 1974, 745–748, XP002102778).

The same article reports reactions of lithium with thiophene to form thienyllithium in the presence of various arenes such as, for example, naphthalene and/or α-methylstyrene. Thus at least 2 mol lithium was required for the preparation of 1 mol thienyllithium in the presence of an approximately stoichiometric quantity of naphthalene. The remaining lithium, or lithium dihydronaphthalenide, was used up by secondary reactions. In Example 3 of the cited literature reference (p. 748), the metalation was carried out in the presence of a large excess of thiophene. The yield of thienyllithium was 41% based on lithium used and less than 20% based on thiophene used.

The reaction of preformed lithium dihydronaphthalenide with excess thiophene (Example 4, p. 748) likewise resulted in poor product yields: 52% based on the lithium reagent and 8% based on thiophene. The product yield in the reaction of lithium dihydronaphthalenide with thiophene could be improved by admixing certain hydrocarbons such as 1,1-diphenylethylene or α-methylstyrene. In Example 5 (p. 748) the yield based on the lithium reagent was 95%, a distinct increase. However, a large excess (300% to 500%) of thiophene was used and consequently the metalation yields based on thiophene were below 50%. The molar quantity of the auxiliary reagent diphenylethylene or α-methylstyrene also exceeded the quantity of lithium or of lithium naphthalenide by a factor of at least 1.5.

The disadvantages of the syntheses described by von Screttas are in general the extremely poor to moderate yields based on the lithium reagent and/or, in particular, based on thiophene. Moreover, the reactions with lithium dihydronaphthalenide are two-step syntheses in which, in the first step, it is necessary to prepare the unstable and not easily handled lithium dihydronaphthalenide which, in a second step, is reacted with thiophene. In all the cases described, large quantities of useless secondary products, namely naphthalene and, optionally, decomposition products are formed in the reactions.

The secondary reactions and unwanted secondary products observed when metals are used can be avoided if organometallic compounds such as butyllithium are used as metalating reagents. However, butyllithium and other lithium organyls prepared from alkyl halides or aryl halides have the disadvantage that ultimately only 50% at most of the metal employed for their synthesis can be used for the 5-ring metalation, because in their synthesis according to the equation

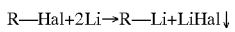

R=alkyl, aryl; Hal=Cl, Br, I

50% of the costly metal is converted into a salt of inferior value (LiHal). They are consequently expensive.

Of particular interest are organolithium syntheses which utilise the lithium as quantitatively as possible and, in a one-step reaction, also allow the best possible yields based on the organic substrate, in this case five-membered heterocycles. Metalated five-membered heterocycles are used very frequently in organic synthesis, as they are indispensable for the synthesis of valuable pharmaceuticals and plant protection products.

The object of the invention is to eliminate the disadvantages of the prior art and to provide a method which, starting from metallic lithium, permits the direct, i.e. one-step, lithiation of CH-acidic five-membered heterocycles with high yields (for example, 70% and more) and makes it possible for the introduced metal to be utilised as quantitatively as possible for the deprotonation, without the formation of useless secondary products such as, for example, alkali halides. Moreover, the process is to proceed selectively, i.e. only certain CH functions of the heterocycle are to be metalated and there is to be no hydrogenation of the C=C double bonds present in the heterocycle.

This object is achieved by the method given in claims 1 and 2. Claims 3 to 13 give further particulars of the given method. Claims 14 and 15 give a particularly advantageous use of the compounds produced by the method according to the invention.

In order to lithiate CH-acidic five-membered heterocycles having a $pK_a$ value of 30 to 40, the five-membered heterocycle is reacted with metallic lithium in an ether-containing solvent in the presence of a hydrogen acceptor (H acceptor).

The method according to the invention proceeds from the method given in DE 19725192, in which the direct metalation of CH-acidic compounds containing one or more CH structural elements having $pK_a$ values of between 10 and 30 is described. Surprisingly, it has now been found that considerably less acidic electron-rich five-membered heterocycles having a $pK_a$ value of >30 can also be metalated with a good yield through a suitable choice of the reactants and of the reaction conditions. It has further been found that where the hydrogen acceptors according to the invention are used, the product yields of >50% up to nearly 100% are distinctly higher than the 41% obtained with the use of naphthalene or lithium naphthalenide.

The CH-acidic five-membered heterocycles used are compounds which contain as ring members, in addition to at least one acidic CH group, a maximum of 4 hetero elements selected from O, S, N and Se. These are five-membered heterocycles containing one hetero atom such as e.g.

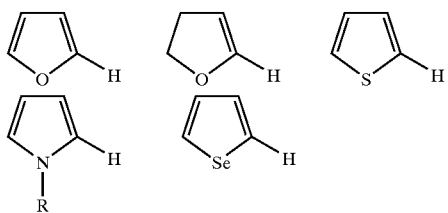

five-membered heterocycles containing two hetero atoms such as e.g.

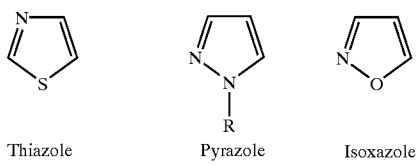

Thiazole  Pyrazole  Isoxazole five-membered heterocycles containing three hetero atoms such as e.g.

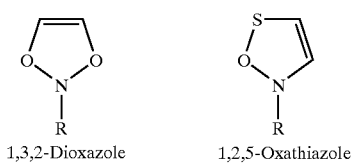

1,3,2-Dioxazole  1,2,5-Oxathiazole or five-membered heterocycles containing four hetero atoms such as e.g.

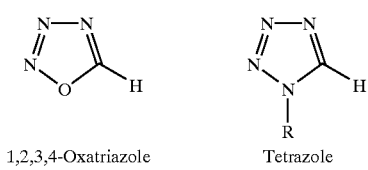

1,2,3,4-Oxatriazole  Tetrazole wherein R=H, alkyl, aryl,

All the above compounds can also be partially substituted, except those species which, apart from the CH-acidic hydrogen atom, do not contain any other hydrogen atom in the five-membered ring.

Particularly suitable CH-acidic five-membered heterocycles are those 5-membered ring systems which have at least one olefinic CH group in the a-position to a hetero atom, selected from O, S, N, Se. Here the C atom of the CH-acidic group is $sp^2$-hybridised.

The CH acidity of the five-membered heterocycles has a $pK_a$ value preferably of about 30 to 40. Some data are shown in the Table below.

TABLE 1

CH acidities

| Compound | | $pK_a$ values in cyclohexylamine |
|---|---|---|
| Benzene (for comparison) | | 43 |
| | X = S | 38.4 |
| | X = O | 38.1 |
| | X = N—Me | ca.: 38–40 |
| | X = S | 37.1 |
| | X = O | 36.8 |
| | | 29.5 |
| | | 28.1 |

In the reaction according to the invention, a hydrogen atom of the acidic five-membered heterocycle is exchanged for a lithium atom. The released hydrogen is taken up by a suitable H acceptor. At the same time the singly hydrogenated monomer and/or the hydrodimerisation product are formed as well as, to a lesser extent, higher oligomers of the hydrogenation product. Where isoprene is used, analysis by gas chromatography indicates, for example, the formation of isopentene as well as of a mixture of various dimethyloctadienes and a small proportion of higher oligomers.

Acyclic or cyclic dienes serve as suitable H acceptors, with 1,3-dienes such as, for example, butadiene, isoprene or 1,3-cyclohexadiene being preferred. It has been found that 1-arylolefins, such as styrene, methylstyrene or 1,1-diphenylethene, do not produce satisfactory results in all cases. The use of 1-arylolefins as H acceptors is limited to the lithiation of relatively acidic five-membered heterocycles (such as, for example, thiazole or other multiply heterosubstituted five-membered rings). If 1-arylolefins are used for the metalation of less acidic compounds such as, for example, thiophene or indole, the yields are distinctly poorer than those obtained with the use of 1,3-dienes.

The H acceptor is used in a quantity of 0.2 to 3 mol, preferably 0.4 to 1.5 mol, per mol of five-membered heterocycle. In most cases an H acceptor in a quantity of 0.5 to 1.2 mol per mol of five-membered heterocycle has proved advantageous.

The lithium metal used for the metalation should preferably be in finely divided form, i.e. as powder having particle sizes of <0.1 mm. However, coarser forms, for example, granulated material having edge lengths of several mm, may also be used. But the reaction times are then longer and the reaction yields generally poorer, unless the coarsely granulated lithium is used in excess. The lithium is typically used in a quantity of 0.5 to 3 mol, preferably 1 to 1.5 mol, per mol of five-membered heterocycle. Where finely divided lithium is used, a largely stoichiometric quantity of 0.95 to 1.1 mol Li per mol of five-membered heterocycle is sufficient.

The solvents used are open-chain or cyclic monethers, in particular tetrahydrofuran (THF) or methyl tert.-butyl ether (MTBE), or polyethers such as, for example, 1,2-dimethoxyethane (1,2-DME) or diethylene glycol dimethyl ether. These can be in pure form or mixed with one another or mixed with hydrocarbons such as, for example, pentane, hexane, cyclohexane, methylcyclohexane, heptane, octane, toluene or ethylbenzene. As hydrocarbons are in general markedly less expensive than ethereal solvents, a proportion of hydrocarbon in the solvent signifies an increase in the economic efficiency of the method according to the invention.

It has been observed that in a few instances, in particular in the case of the less CH-acidic five-membered heterocycles such as, for example, 2,3-dihydrofuran, the start of the reaction is delayed and/or it produces only moderate yields. In these cases, in particular, it is advisable to activate the metal by a known method. A particularly suitable method for this is the addition of a metal phase transfer catalyst, referred to below as a phase transfer catalyst (PTC), such as, for example, naphthalene, anthracene, diphenyl or di-tert.-butyldiphenyl. In anhydrous polar-aprotic solvents, the aforementioned polycyclic aromatics are able to add lithium with the formation of radical-anionic complexes. The oxide film on the metal is thereby broken up and lithium is converted into a highly reactive, soluble form. In this way the aforementioned catalysts lessen the unwanted induction phase; moreover, the result of their presence in the reaction mixture is that less H acceptor is required in order to achieve a given product yield. The quantity of PTC added is typically 0 to 0.2 mol, preferably 0 to 0.1 mol, per mol of five-membered heterocycle.

The experimental procedure is generally as follows:

First of all, the lithium metal is suspended in the anhydrous, aprotic solvent or mixture of solvents. The five-membered heterocycle to be metalated is then added to the suspended metal. The reverse procedure (i.e. addition of the Li suspension or of the lithium to the solution of the five-membered heterocycle) is in principle also possible, but this variant has proved to be more complicated technically.

The metalation reaction is then initiated by adding the H acceptor. Where a phase transfer catalyst is used, it can be added in various ways. It is particularly advantageously added together with the lithium. It can also be introduced in a mixture with the H acceptor.

The most favourable reaction temperatures are generally between 0° C. and 60° C., with thermally labile solutions of the product being obtained at lower temperatures. Higher temperatures tend to result in decomposition of the product; lower temperatures, owing to their higher energy consumption, tend to be less economic.

The times taken to introduce the reagents are between about 15 minutes and several hours, depending on the five-membered heterocycle and on the cooling capacity. When the addition of the H acceptor is complete there is a subsequent reaction stage, which generally takes 15 minutes to 4 hours. On conclusion of the subsequent reaction, the reaction mixture is filtered in order to remove unreacted metal and small quantities of insoluble secondary products.

The yields of selectively lithiated five-membered heterocycle which can be attained by this method depend on the CH acidity and on reaction-specific variables (for example, type of solvent, stoichiometry, use of catalyst) and are between 30% and almost 100%.

A solution of the product containing approximately 5 to 25 wt. % of the lithiated five-membered heterocycle, hydrogenated dimers and oligomers of the H acceptor and optionally traces of the PTC is obtained.

It was observed that some of the solutions of the product prepared according to the invention, for example, 2-furanyllithium, in pure ethereal solvents are insufficiently stable in storage. Whereas, for example, an approximately 11 wt. % 2-furanyllithium solution having a molar ratio of 2-furanyl-Li:THF of approximately 1:7 at 25° C. decomposes at a rate of about 10% per day, the decomposition rate for a similar 11 wt. % 2-furanyllithium solution in which a part of the THF has been replaced by a hydrocarbon (for example, toluene or cyclohexane) and which has a molar ratio of 2-furanyl-Li:THF of approximately 1:1 is only 0.12% per day. A solution of 2-furanyllithium which is low in THF is therefore far more stable and can be stored and transported for a longer period and without elaborate cooling methods.

The solutions of the final product such as, for example, 2-lithiofuran, referred to below as furanyllithium, or 2-lithiothiophene, referred to below as thienyllithium, can be derivatised by reaction with electrophilic reagents such as, for example, carbonyl compounds, oxiranes, sulfur, carbon dioxide or alkyl halides. These products have a variety of uses in organic chemistry, in particular as intermediates for the preparation of pharmaceuticals and plant protection products.

The subject matter of the invention is explained in more detail below by means of Examples.

EXAMPLES 1 TO 10

Examples 1 to 10 (shown in Table 2) demonstrate the preparation of 2-thienyllithium from thiophene by means of different variants of the method. Thiophene, with a $pK_a$ value of 38.4, is only slightly more acid than toluene (40.9). In Examples 1 to 5 and 7 to 10 the procedure was in accordance with the following general operating instructions:

The lithium powder (particle size <0.1 mm) was suspended in the given solvent and a phase transfer catalyst (PTC) was optionally added thereto. After addition of 68 g (1.0 mol) of thiophene, the respective H acceptor was added dropwise (styrene, isoprene) or passed in (butadiene) over a period of 1 to 2 hours. After a subsequent reaction time of 0.5 to 4 hours, the reaction mixtures were clarified by filtration and the yield was determined by means of base titration or by means of quantitative gas chromatography (GC). Here 2-trimethylsilylthiophene (after derivatisation of the product with trimethylchlorosilane) was measured in the GC.

In Example 6 the procedure was similar. However, the phase transfer catalyst was not introduced beforehand in the solvent, but added together with the H acceptor.

TABLE 2

Preparation of 2-thienyllithium

| | Molar ratio[1] | | | Mol solvent | Prepn. | Yield (%) | |
|---|---|---|---|---|---|---|---|
| Ex. | Li | H acceptor[2] | PTC[1)3)] [mol %] | per mol thiophene | temp.[4] [° C.] | Total base[5] | GC[6] |
| 1 | 0.95 | 0.49 S | / | 3.0 THF | ca. 25 | 5 | 3 |
| 2 | 0.99 | 0.49 S | 6.9 N | 3.0 THF | ca. 25 | 73 | 47 |
| 3 | 1.1 | 0.58 I | / | 6.6 THF | 25/50 | 56 | 61 |
| 4 | 0.97 | 0.61 I | 1.0 N | 6.9 THF | ca. 23 | 70 | 73 |

TABLE 2-continued

Preparation of 2-thienyllithium

| | Molar ratio[1] | | | Mol solvent per mol thiophene | Prepn. temp.[4] [°C.] | Yield (%) | |
|---|---|---|---|---|---|---|---|
| Ex. | Li | H acceptor[2] | PTC[1)3] [mol %] | | | Total base[5] | GC[6] |
| 5 | 0.97 | 0.62 I | 3.1 N | 6.9 THF | ca. 23 | 93 | 82 |
| 6 | 1.1 | 0.60 I | 3.1 A | 6.7 THF | 25/50 | 65 | 61 |
| 7 | 0.97 | 0.63 I | 2.9 N | 2.0 THF/ 4.1 cyclohexane | ca. 23 | 84 | 80 |
| 8 | 0.97 | 0.75 I | 2.0 N | 2.0 THF/ 3.1 toluene | 35 | 93 | / |
| 9 | 0.96 | 0.59 I | 3.0 N | 5.3 1,2-DME | ca. 23 | 78 | / |
| 10 | 0.94 | 1.0 B | / | 2.0 THF/ 2.8 toluene | ca. 10 | 87 | 90 |

[1]Thiophene = 1;
[2]S = styrene; I = isoprene; B = 1,3-butadiene;
[3]N = naphthalene; A = anthracene;
[4]Pre-/post reaction;
[5]Total quantity of base in solution;
[6]Determination by gas chromatography as 2-trimethylsilylthiophene The conclusions from Table 2 are as follows:

If styrene is used as H acceptor and the procedure is carried out without phase transfer catalyst (PTC), 2-thienyllithium is obtained only in very low yield (<5% Example 1). Under identical conditions, the addition of 6.9 mol % naphthalene as PTC results in a marked increase in yield (Example 2). If isoprene is used instead of styrene, even without PTC a product yield of >50% is achieved (Example 3).

On the simultaneous addition of naphthalene as PTC, a further increase in yield is recorded (Examples 4 and 5). Other polycyclic aromatics, for example, anthracene (Example 6), can also be used instead of naphthalene as PTC.

The relatively costly THF can be partially replaced by cheaper hydrocarbons such as cyclohexane or toluene, without any observable adverse effect on the yield (Examples 7 and 8). But at least 2 mol of an ethereal solvent, preferably THF, per mol of 2-thienyllithium should be present in the solution of the product, in order to obtain solutions which are non-crystallising.

Instead of being introduced beforehand, the PTC can also be added together with the H acceptor (Example 8). Example 9 describes the use of 1,2-dimethoxyethane as a reaction solvent. Example 10 shows that when a larger quantity of H acceptor is used (in this case, 1,3-butadiene), very good product yields can be achieved even without the use of PTC.

EXAMPLES 11 TO 16

Examples 11 to 16 (shown in Table 3) demonstrate the lithiation of various five-membered heterocycles. Here the procedure was in accordance with the following general operating instructions:

The lithium powder (particle size <0.1 mm) was suspended in the given solvent, the phase transfer catalyst naphthalene was added thereto and, after the initial appearance of the green coloration, 0.5 mol of the respective CH-acidic five-membered heterocycle was added. The H acceptor isoprene was then added dropwise over a period of 1 to 2 hours. After a subsequent reaction time of approximately 1 hour, the reaction mixture was clarified by filtration. The product, after derivatisation with methyl iodide, was characterised by gas chromatography (GC) and mass spectroscopy (MS) and the yield was determined by means of base titration.

TABLE 3

Lithiation of various five-membered heterocycles

| | | Molar ratio[1] | | | Solvent | | |
|---|---|---|---|---|---|---|---|
| Ex. | Hetero-cycle | Li | Iso-prene | PTC[1)2] (mol %) | Mol/Mol heterocycle | Derivatisation product[3] | Yield (%)[4] |
| 11 | | 0.91 | 0.66 | 3 | 0.9 THF/ 5.3 toluene | 2-Me-furan | 97 |
| 12 | | 0.90 | 0.68 | 1 | 0.9 THF/ 5.9 toluene | 2-Me-furan | 65 |
| 13 | | 1.00 | 0.99 | 3 | 6.1 THF | 2-Me-dihydrofuran | 60 |
| 14 | | 0.95 | 0.98 | 2.9 | 5.5 1,2-DME | 1,2-dimethyl-pyrrole | 82 |
| 15 | | 1.00 | 1.03 | 3.2 | 12.0 THF | 1,2-dimethyl-indole | 69 |
| 16 | | 1.00 | 0.51 | 2.9 | 8.7 THF | / | 86 |

[1]Heterocycle = 1;
[2]PTC = naphthalene
[3]Reaction with methyl iodide and identification by GC/MS;
[4]Determination of the alkalinity of the solution by filtration The conclusions from Table 3 are as follows:

Furan can be lithiated with very good yields, and naphthalene promotes product formation (Examples 11 and 12). The less acidic 2,3-dihydrofuran produces smaller yields, although more H acceptor was used (Example 13). N-methylpyrrole in 1,2-dimethoxyethane reacts to produce 2-lithio-N-methylpyrrole in good yields (Example 14).

N-methylindole is lithiated in THF with satisfactory yields (Example 15). Even a small quantity of hydrogen acceptor suffices for the lithiation of the relatively acidic 4-methylthiazole (Example 16).

What is claimed is:

1. Method of lithiating CH-acidic five-membered heterocycles, wherein the five-membered heterocycle is reacted with metallic lithium in an ether-containing solvent in the presence of an H acceptor, and the CH-acidic bond of the five-membered heterocycle has a pK$_a$ value of 30 to 40 and the H acceptor is an open-chain, unsubstituted or substituted

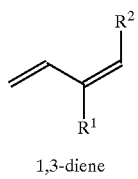

1,3-diene wherein $R^1$, $R^2$ =H, alkyl, vinyl,
wherein $R^1$, $R^2$ in cis or trans configuration
or a cyclic 1,3-diene

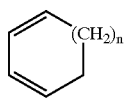

wherein
  n=1 to 5
  and is used in a quantity of 0.2 mol to 3 mol per mol of five-membered heterocycle.

2. Method of lithiating CH-acidic substituted five-membered heterocycles, wherein the five-membered heterocycle is reacted with metallic lithium in an ether-containing solvent in the presence of an H acceptor, and the CH-acidic bond of the five-membered heterocycle has a $pK_a$ value of 30 to 40 and the H acceptor is an open-chain, unsubstituted or substituted 1,3-diene,
or a cyclic 1,3-diene,
or an unsubstituted or substituted 1-arylolefin

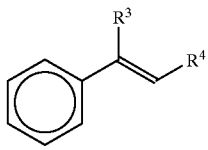

wherein
$R^3$, $R^4$=H, alkyl of 1 to 5 C atoms wherein $R^3$, $R^4$ in cis or trans configuration
and is used in a quantity of 0.2 mol to 3 mol per mol of five-membered heterocycle.

3. The method of claim 1 wherein the five-membered heterocycle includes at least one ring hetero atom selected from the group consisting of O, S, N or Se and at least one CH-acidic group in the α-position to said hetero atom and wherein the C atom of the CH-acidic group is sp-hybridized.

4. The method of claim 1 wherein the five-membered heterocycle is furan, 2,3-dihydrofuran, thiophene or pyrrole and wherein the five-membered heterocycle is substituted or unsubstituted, and wherein the five membered heterocycle includes an unsubstituted CH-acidic group situated in the α-position to a ring hetero atom.

5. The method of claim 1 wherein the H acceptor is isoprene, butadiene or 1,3-cyclohexadiene.

6. The method of claim 1 wherein the H acceptor is used in a quantity of 0.4 to 1.5 mol per mol of the five-membered heterocycle.

7. The method of claim 1 wherein the lithium metal is used in finely divided form, as powder having particle sizes of <0.1 mm.

8. The method of claim 1 wherein the solvent comprises one or more open-chain or cyclic ethers, or mixtures of one or more ethers and of one or more hydrocarbons.

9. The method of claim 8 wherein the solvent is THF in pure form or mixed with hydrocarbons.

10. The method of claim 9 wherein the hydrocarbon is pentane, hexane, cyclohexane, methylcyclohexane, heptane, octane, toluene or ethylbenzene.

11. The method of claim 1 wherein the reaction is carried out in the presence of a metal phase transfer catalyst, the metal phase transfer catalyst being used in a quantity of up to 0.2 mol per mol of five-membered heterocycle.

12. The method of claim 11 wherein the metal phase transfer catalyst is a polycyclic aromatic.

13. The method of claim 12 wherein the polycyclic aromatic is naphthalene, anthracene, diphenyl or di-tert.-butyldiphenyl.

* * * * *